United States Patent
Grant (10) Patent No.: US 7,374,876 B2
(45) Date of Patent: May 20, 2008

(54) ANTI-IDIOTYPIC ANTIBODY AND ITS USE IN DIAGNOSIS AND THERAPY OF HEPATITIS C VIRUS RELATED DISEASES

(75) Inventor: Michael D Grant, St. John's (CA)

(73) Assignee: Rapid Medical Diagnostic Corporation, Miami Beach, FL (US)

( * ) Notice: Subject to any disclaimer, the term of this patent is extended or adjusted under 35 U.S.C. 154(b) by 0 days.

(21) Appl. No.: 10/474,296

(22) PCT Filed: Apr. 2, 2002

(86) PCT No.: PCT/CA02/00416

§ 371 (c)(1),
(2), (4) Date: Mar. 11, 2004

(87) PCT Pub. No.: WO02/082089

PCT Pub. Date: Oct. 17, 2002

(65) Prior Publication Data

US 2004/0146857 A1    Jul. 29, 2004

Related U.S. Application Data

(60) Provisional application No. 60/281,280, filed on Apr. 3, 2001.

(51) Int. Cl.
*C12Q 1/00* (2006.01)
*C12Q 1/70* (2006.01)
*G01N 33/53* (2006.01)

(52) U.S. Cl. .................. 435/5; 435/4; 435/7.1

(58) Field of Classification Search ............ 424/130.1, 424/131.1, 141.1, 147.1, 148.1, 149.1, 159.1, 424/160.1, 161.1; 435/4, 5, 7.1, 29, 34; 530/300, 530/350, 387.1, 387.2, 388.1, 388.2, 388.5, 530/388.35
See application file for complete search history.

(56) References Cited

U.S. PATENT DOCUMENTS

| | | | |
|---|---|---|---|
| 5,849,583 | A | 12/1998 | Müller et al. |
| 6,146,627 | A | 11/2000 | Müller et al. |
| 6,692,908 | B1 * | 2/2004 | Foung et al. ............ 435/5 |
| 2002/0090607 | A1 * | 7/2002 | Fields et al. ............ 435/5 |
| 2003/0186269 | A1 | 10/2003 | Bahr et al. |

FOREIGN PATENT DOCUMENTS

| EP | WO 94/14974 | * 7/1994 |
|---|---|---|
| WO | WO 00/26418 | * 11/2000 |
| WO | WO 01/88128 A1 | 11/2001 |

OTHER PUBLICATIONS

Wang et al., "Identification of an idiotypic peptide recognized by autoantibodies in human immunodeficiency virus-1-infected individuals," Journal of Clinial Investigation, vol. 96 No. 2, pp. 775-780 (Aug. 1995).*
Mizorogi et al., "Hepatitis C virus infection in patients with B-cell non-Hodgkin's lymphoma," Internal Medicine, vol. 39 No. 2, pp. 112-117 (Feb. 2000).*
Askonas, B. and Williamson, A., "Dominance of a Cell Clone Forming Antibody to DNP," *Nature*, 238:339-341 (Aug. 1972).
Bain, Allen, "Immune Network Initiates Hepatitis C Research," *News Bites, Online!*, <www.askemilyss.com/bites/bite0300/imm.htm> (Jun. 24, 2002).
Bebenek, K. et al., "Specificity and Mechanism of Error-Prone Replication by Human Immunodeficiency Virus-1 Reverse Transcriptase," *J. Biol. Chem.*, 264:16948-16956 (Oct. 5, 1989).
Berberian, L. et al., "Immunoglobuling $V_h3$ Gene Products: Natural Ligands for HIV gp120," *Science*, 261:1588-1591 (Sep. 1993).
Blank, M. et al., "The Importance of the Pathogenic 16/6 Idiotype in the Induction of SLE in Naive Mice," *Scand. J. Immunol.*, 31:45-52 (1990).
Briles, D. and Davie, J., "Clonal Nature of the Immune Response," *J. Exp. Med.*, 152:151-160 (Jul. 1980).
Chen, M. et al., "Limited Humoral Immunity In Hepatitis C Virus Infection," *Gastroenterology*, 116:135-43 (Jan. 1999).
Cohen, Irun, "The Cognitive Paradigm and the Immunological Homunculus," *Immunol. Today*, 13:490-494 (1992).

(Continued)

*Primary Examiner*—Z. Lucas
(74) *Attorney, Agent, or Firm*—Townsend and Townsend and Crew LLP (57) ABSTRACT

The present invention provides methods for the diagnosis, prognosis and treatment of HCV-related disease. The method takes advantage of a novel reactive mechanism of the murine monoclonal antibody (mAb) 1F7 against human antibodies specific for different proteins of the Hepatitis C Virus (HCV) and Human immunodeficiency virus (HIV). 1F7 recognizes antibodies against HCV core protein in a majority of HCV-infected individuals and antibodies against HCV non-structural proteins 3 (NS3) and NS4 in some HCV-infected individuals. 1F7 also recognizes antibodies against the putative principle neutralizing determinant (hypervariable and conserved region 1 of the HCV E2 protein) of HCV. The antibody can be used in various methods to detect HCV related disease and formulated with physiologically acceptable carriers in various compositions to treat HCV infection.

5 Claims, 3 Drawing Sheets

OTHER PUBLICATIONS

Grant, M. et al., "Distribution of Antibodies Against Denatured Collagen in AIDS Risk Groups and Homosexual Aids Patients Suggests a Link Between Autoimmunity and the Immunopathogenesis of AIDS," *J. Immunol.*, 144:1241-1250 (Feb. 1990).

Grant, M. et al., "Similar Abnormalities of Idiotype and Immunoglobulin Light Chain Expression and of Cell-Mediated Cytotoxicity in HIV-Infected Humans and Simian Immunodeficiency Virus (Siv)-Infected Rhesus Macaques," *Immunol. Cell Biol.*, 74:38-44 (1996).

Grant, Michael, "Antibody Convergence Along a Common Idiotypic Axis in Iinmunodeficiency Virus and Hepatitis C Virus Infections," *J. Med. Virol.*, 66:13-21 (2002).

Kang, C. et al., "Evidence for Non-V3-Specific Neutralizing Antibodies that Interfere with gp120/CD4 Binding in Human Immunodeficiency Virus 1-Infected Humans," *Proc. Natl. Acad. Sci. USA*, 88:6171-6175 (Jul. 1991).

Kennedy, R. and Dreesman, G., "Antigen Mimicry by Anti-Idiotype Antibodies that Recognize a Common Anti-Hepatitis B Surface Antigen Idiotype," *Adv. Exp. Med. Biol.*, 185:139-147 (1985).

Köhler, H. et al., "Deceptive Imprinting in the Immune Response Against HIV-1," *Immunol. Today*, 15:475-478 (1994).

Köhler, H. et al., "Why AIDS Vaccines That Induce Humoral Immunity May Not Work," *The Immunologist*, 3:32-33 (1995).

Konikoff, F. et al., "Common Lupus Anti-DNA Antibody Idiotypes in Chronic Liver Diseases," *Clin. Immunol. Immunopathol.*, 43:265-272 (1987).

Mendlovic, S. et al., "In Vitro T-Cell Functions Specific to an Anti-DNA Idiotype and Serological Markers in Patients with Systemic Lupus Erythematosus (SLE)," *J. Clin. Immunol.*, 8:178-187 (1988).

Montefiori, D. et al., "Homotypic Antibody Responses to Fresh Clinical Isolates of Human Immunodeficiency Virus," *Virology*, 182:635-643 (1991).

Müller, S. et al., "Stimulation of HIV-1-Neutralizing Antibodies Insimian HIV-IIIB-Infected Macaques," *Proc. Natl. Acad. Sci. USA*, 95:276-281 (Jan. 1998).

Nara, P. et al., "Absence of Cytotoxic Antibody to Human Immunodeficiency Virus-Infected Cells in Humans and its Induction in Animals After Infection or Immunization with Purified Envelope Glycoprotein gp120," *Proc. Natl. Acad. Sci. USA*, 84:3797-3801 (Jun. 1987).

Nara, P. et al., "Emergence of Viruses Resistant to Neutralization by V3-Specific Antibodies in Experimental Human Immunodeficiency Virus Type 1 IIIB Infection of Chimpanzees," *J. Virol.*, 64:3779-3791 (Aug. 1990).

Nara, P. et al., "Neutralization of HIV-1: a Paradox of Humoral Proportions," *FASEB J.*, 5:2437-2455 (Jul. 1991).

Ogata, N. et al., "Nucleotide Sequence and Mutation Rate of the H Strain of Hepatitis C Virus," *Proc. Natl. Acad. Sci. USA*, 88:33392-3396 (Apr. 1991).

Puntoriero, G. et al., "Towards a Solution for Hepatitis C Virus Hypervariability: Mimotopes of the Hypervariable Region 1 Can Induce Antibodies Cross-Reacting with a Large Number of Viral Variants," *EMBO J.*, 17:3521-3533 (1998).

Schwartz, R. and Stollar, B., "Origins of Anti-DNA Autoantibodies," *J. Clin. Invest.*, 75:321-327 (Feb. 1985).

Shoenfeld, Y. et al., "Production of Autoantibodies by Human-Human Hybridomas," *J. Clin. Invest.*, 70:205-208 (Jul. 1982).

Wang, H. et al., "Human Monoclonal and Polyclonal Anti-Human Immunodeficiency Virus-1 Antibodies Share a Common Clonotypic Specificity," *Eur. J. Immunol.*, 22:1749-1755 (1992).

Webster, R.G., "Original Antigenic SIN in Ferrets: the Response to Sequential Infections with Influenza Viruses," *J. Immunol.*, 97:177-183 (1996).

Zhou, S. et al., "Monoclonal Antibodies to the Hypervariable Region 1 of Hepatitis C Virus Capture Virus and Inhibit Virus Adsorption to Susceptible Cells in Vitro," *Virology*, 269:276-283 (2000).

Zhou, Y. and Whitaker, J., "An Idiotype Shared by Monoclonal Antibodies to Different Peptides of Human Myelin Basic Protein," *J. Immunol.*, 145:2554-2560 (Oct. 1990).

Besson, C. et al., "Lack of association between HCV infection and HIV-related lymphoma," *Br. J. Haematol.*, 105:568-569 (May 1999).

Grant, M. et al., "The anti-idiotypic antibody 1F7 selectively inhibits cytotoxic T cells activated in HIV-1 infection," *Immunol. Cell Biol.*, 78:20-27 (Feb. 2000).

* cited by examiner

ANTI-IDIOTYPIC ANTIBODY AND ITS USE IN DIAGNOSIS AND THERAPY OF HEPATITIS C VIRUS RELATED DISEASES

BACKGROUND OF THE INVENTION

The present invention provides methods and compositions for the diagnosis, monitoring, and modulation of the immune response to Hepatitis C Virus (HCV) related diseases. The methods take advantage of a novel reactive mechanism of the murine monoclonal antibody (mAb) 1F7 against human antibodies specific for different proteins of the Hepatitis C virus (HCV). In particular, the antibodies recognize HCV core protein in a majority of HCV-infected individuals and antibodies against HCV non-structural proteins 3 (NS3) and NS4 in some HCV-infected individuals. Also, the antiidiotypic antibody recognizes antibodies against the putative principle neutralizing determinant (hypervariable region 1 of the HCV E2 protein) of HCV. The idiotypic linking of antibodies against multiple epitopes of a chronic pathogen provides methods for improved diagnosis and monitoring of HCV as well as opportunities to increase the efficiency of immune regulation, including limiting "idiotypic "grid-lock", that can arise from chronic antigenic stimulation.

Hepatitis C virus (HCV) is a plus sense RNA virus that establishes chronic infection in up to 80% of exposed individuals. Long-term infection can lead to liver cirrhosis and hepatocellular carcinoma. Currently, no effective vaccine or treatment for HCV infection is available. The ability of HCV to mutate key immunological determinants and to escape immune selection pressures exerted by antibodies and T cells in an infected individual is important for the establishment of chronic infection. Similar to HLV infection, the immune system can become locked into recognition of the original infecting strain of HCV and therefore is unable to adapt to, and recognize, subsequent mutations. Antibodies against a particular region of HCV E2 protein, hypervariable region 1 (HVR1) are believed to be important to preventing new infection of cells and promoting clearance of viral particles. An antibody response directed against a broad range of HCV epitopes in addition to HCV E2 HVR1 would be expected to provide better protection against HCV mutants and to be associated with a more favorable clinical outcome to infection.

Although HCV and HIV are genetically unrelated and the viruses have a different pattern of cellular tropism and induce distinct diseases, HCV and HIV share important features relevant to their interactions with the immune system of the infected host. In particular, both viruses commonly establish chronic infections, thought at least in part, to be due to RNA polymerases characterized as "mistake-prone" that generate a high mutation rate during viral replication (Bebenek et al., *J. Biol. Chem.* 264:16948-16956 (1989); Ogata et al., *Proc. Natl. Acad. Sci USA* 88:3392-3396 (1991). These mutations produce viral variants which can undergo immune selective pressures in the infected host. The selective pressures favor the outgrowth of those viral variants poorly neutralized by the anti-viral antibodies concurrently present in the host. Therefore, the less diverse the neutralizing response to the infecting virus, the more easily viral escape occurs through random mutations within neutralization epitopes. Since random mutations cannot be anticipated by the immune system, adaptation of the immune response lags behind the virus resulting in chronic infection.

Mutating viruses also exploit a phenomenon known as "original antigenic sin", wherein the immune system commits itself to responding to the viral variant initially present and continues to make antibodies against the image of this virus variant even when the virus present has effectively shed that image (Webster, *J. Immunol.* 97:177-183 (1996)). although some level of cross-reactivity with emergent viruses may explain persistence of the seminal antibodies, the mechanism which stops the immune system of the infected host from producing high affinity neutralizing antibodies against emergent viral variants is not clear.

In the case of HIV infection, "original antigenic sin" manifests as B cell clonal dominance, where the original responding B cells are "locked in" through a process termed "deceptive imprinting" or a repertoire freeze" (Kohler et al., *Immunol. Today* 15:475-478 (1994). This clonal dominance involves restricted diversity in the set of antibodies produced against HIV and apparently can weaken the adaptation of the immune response to emerging mutants and favor viral persistence. In addition, clonal dominance has been associated with the expression of a common idiotype on anti-HIV antibodies with different specificities (Kohler et al., *Immunol. Today* 15:475-478 (1994); Kohler et al., *Immunologist* 3:32-34 (1995)). Expression of a common idiotype on antibodies against a particular antigen may therefore be associated with a narrow antibody response against that antigen.

Antibodies with common patterns of auto-reactivity have also been found to have emerged in other chronic inflammatory conditions including HIV, systemic lupus erytnematosus (SLE), graft-versus-host disease, and lepromatous leprosy (Grant et al., *J. Immunol.* 144:1241-1250 (1990)). this has suggested that the immune system is predisposed to respond along certain autoreactive axes when chronically stimulated by an antigen. There has been speculation that chronic pathogens can selectively activate responses along auto-reactive axes to divert the immune system from mounting a more effective anti-microbial response. If true, there can be therapeutic value in steering the immune response in an infected host away from producing antibodies specific for epitopes delineated by such fruitless axes.

An idiotope common to more than one type of HIV-1 antibody has been discovered (U.S. Pat. No. 5,849,583, incorporated herein by reference in its entirety). The idiotope is common to antibodies produced by restricted B cell clones and has been found to be specifically reactive with at least three anti-HIV antibodies having separate specificities. One particular anti-idiotypic antibody reactive with this idiotope is the mureine monoclonal antibody 1F7. To date, the 1F7 idiotype has been found on antibodies against 2 chronic pathogens, HIV and SIV, suggesting that both selectively activate antibodies along a particular idiotype axis or that chronic stimulation itself drives selection of the 1F7 idiotype. Since uninfected volunteers receiving HIV gp120 vaccination express the 1F7 idiotype on their anti-HIV antibodies, the idiotype appears to be selected in the initial response to HIV and to persist throughout infection.

In the SIV model of HIV infection, administering 1F7 to SHIV-infected animals expressing the 1F7 idiotype on their anti-SHIV antibodies "thawed" the frozen B cell repertoire. Relief from clonal dominance was illustrated by a broadening of the HIV neutralizing antibody response to encompass viruses distinct from the inoculating strain together with an increase in neutralization titer against the inoculating strain.

Shared idiotypic determinants on antibodies reflect genetic relatedness between variable (V) gene segments, common antigenic specificities or overlapping idiotype-based immunoregulatory pathways. The anti-idiotypic antibody 1F7 has been identified to recognize antibodies against different HIV and SIV proteins in approximately 70% of HIV-infected humans and SIV-infected macaques. As the 1F7 idiotype is neither restricted to antibodies expressing the same heavy chain V gene family, nor to antibodies recognizing structurally homologous antigens, it was proposed that antibodies against distinct antigens of chronic pathogen (s), such as HIV, HCV and related disease causing agents, are selected for expression of a common regulatory idiotypic target. The idiotypic linking of antibodies against multiple epitopes of a chronic pathogen can increase the efficiency of immune regulation and limit idiotypic gridlock that might arise from chronic antigenic stimulation.

The presence of 1F7 idiotype on such a diverse set of antiviral antibodies illustrated that B cells expressing $Ab_2$ recognizing the 1F7 idiotype had very high connectivity within the B cell repertoire. Such high connectivity would tend to suppress activation of the regulatory $Ab_2$-bearing B cells and favor assumption of clonal dominance by the responding 1F7 idiotype$^+$ B cells.

A somewhat analogous situation was previously reported with regard to the 16/6 idiotype, which unlike 1F7 is associated with a particular heavy chain V gene family. The 16/6 idiotype was first defined on a monoclonal anti-DNA antibody and later on other auto-antibodies and anti-microbial antibodies. Expression of this idiotype is associated with systemic lupus erythematosus (SLE) in humans and injection of antibodies bearing this idiotype into mice induced SLE-like symptoms. Pathogenic immune complexes in both situations contain 16/6 idiotype$^+$ antibodies, fueling speculation that 16/6 can act as a pathogenic idiotype to perturb the regulatory network in such a way as allows autoimmunity to develop.

However, the probability of chronic pathogens evolving determinants on so many individual proteins to take advantage of this structural feature of B cell networks seems remote. One alternative possibility is that the initial antibody response to HIV gp120 represents a special case, by virtue of gp120 acting as a B cell super-antigen. Investigators showed that gp120 binds a broad set of immunoglobulin molecules based on the heavy chain V gene family expressed. Such polyclonal activation would assure activation of clones expressing the 1F7 Idiotype and the high connectivity of the potential regulatory anti-idiotype would free the 1F7$^+$ B cells to establish clonal dominance.

This proposed pattern of idiotypic focusing could have adaptive as well as negative implications for the immune system. While freezing potential neutralizing antibody responses against a mutating pathogen is clearly a disadvantage, localizing chronic B cell activation within a limited region of idiotypic space could protect against immunopathology and leave a more extensive B cell repertoire free to respond against unrelated pathogens. It remains to be determined how widespread 1F7 idiotype expression is on antibodies against other chronic pathogens and on autoantibodies.

What is needed in the art are additional methods for diagnosis, monitoring and treatment of Hepatitis C virus related disease which improve the immunologic response to the variations in the infectious variant and prevents chronic infection.

BRIEF SUMMARY OF THE INVENTION

The present invention provides methods and compositions for the diagnosis, monitoring and treatment of Hepatitis C Virus (HCV)-related disease. In particular, the methods use anti-idiotypic antibodies specifically reactive with an idiotope common to more than one type virus which can lead to a chronic infection. In one embodiment of the invention the anti-idiotypic antibodies useful in the methods of the present invention are reactive with antibodies specifically immunoreactive with more than one antigen of human Hepatitis C. In particular, the invention provides methods which use a composition comprising an anti-idiotypic antibody which is specifically reactive with more than one type of human anti-HCV antibody, and not specifically reactive to antibodies which are not reactive with HCV antigens.

In one embodiment a method is provided for the detection of Hepatitis C Virus (HCV)-related pathologies comprising detecting the expression of an idiotope recognized by an anti-idiotypic antibody having specific reactivity with anti-idiotope common to antibodies reactive with viruses which lead to a chronic infection on the immunoglobulins of a Hepatitis C Virus infected individual. In one particular embodiment of the present invention the idiotope is recognized by the murine monoclonal antibody designated 1F7, which is specifically reactive against at least three human anti-HCV antibodies of differing specificities, and non-reactive with human non-HCV antibodies. A particular HCV-related pathology which can be detected by the methods of the present invention is HCV-related B cell lymphoma.

In another embodiment of the present invention methods are provided for monitoring the progression of an HCV-related pathology comprising detecting the expression of an idiotope recognized by an anti-idiotypic antibody having specific reactivity with anti-idiotope common to antibodies reactive with viruses which lead to a chronic infection on the immunoglobulins of a Hepatitis C Virus infected individual over a defined period of time. Anti-idiotypic antibodies of particular use are those recognized by anti-idiotypic antibodies specific for antibodies reactive with HIV, SIV and HCV. In a typical embodiment of the present invention the idiotope is recognized by the murine monoclonal antibody designated 1F7, which is specifically reactive against antibodies reactive with HIV and also reactive with at least three human anti-HCV antibodies of differing specificities, and non-reactive with human non-HCV antibodies. A particular HCV-related pathology which can be detected by the methods of the present invention is HCV-related B cell lymphoma.

The 1F7 antibody has also been shown to influence T cell anti-idiotypic regulation. Therefore, the present invention provides a method of regulating the immune response in HCV-infected individuals through administration of an effective amount of the anti-idiotypic antibody 1F7 antibody, fragments and derivatives thereof. The antibody, fragments and derivatives thereof are thought to be effective through the selective binding of subsets of B and T lymphocytes by the antibody, fragments, derivatives of the present invention.

In addition, the presence of the idiotope recognized by the anti-idiotope antibody of the present invention in the sera of HCV-infected individuals was found to correlate with HCV-related pathologies. In particular the presence of the epitope was correlated with HCV-related B cell lymphoma. Therefore, methods for the prevention or treatment of HCV-related diseases, including HCV-related B cell lymphoma, comprising administering to an HIV infected individual an effective amount of an anti-idiotypic antibody having a specific reactivity with an idiotope common to antibodies reactive with viruses which lead to chronic infection. The antibodies particularly useful in the method comprise those anti-idiotypic antibodies reactive with an idiotope common to antibodies reactive with the viruses HIV, SIV and HCV.

BRIEF DESCRIPTION OF THE DRAWINGS

FIGS. 1A and 1B depicts the expression of the 1F7 idiotype on anti-HCV core antibodies. FIG. 1A depicts the expression in HIV/HCV co-infected individuals.

DESCRIPTION OF THE SPECIFIC EMBODIMENTS

The present invention provides methods of diagnosis, monitoring and treatment of HCV-related diseases through the use of anti-idiotypic antibody and related compounds which recognize this common idiotope. Expression of a common idiotype on antibodies against a particular antigen may be associated with a narrow antibody response against that antigen; a situation which has been termed "clonal dominance". Clonal dominance can weaken the adaptation of the immune response to emerging viral mutants and favour viral persistence. Elimination of the B cells responsible for clonal dominance allows recruitment of new B cell clones producing antibodies more appropriate for the mutated virus. When the dominant cells share a common idiotype, this can be achieved by administration of anti-idiotypic antibodies against that common idiotype.

In the present invention it has been determined that the a common idiotype that has been reported in association with clonal dominance in HIV infection, as represented by the murine monoclonal antibody 1F7, is expressed on anti-HCV antibodies with different specificities. These new findings regarding the humoral immune response against HCV have significant implications for the pathogenesis of HCV disease and broader implications for the structure and function of idiotypic networks. In the present invention it was speculated that selection of the 1F7 idiotype might spread to anti-HCV antibodies in HIV/HCV co-infected individuals. Instead, surprisingly it was found that the 1F7 idiotype appears on anti-HCV antibodies in non-HIV-infected individuals is instance, administration of 1F7 may break the clonal dominance of ineffective anti-HCV antibodies and promote a broader, more effective antibody response. In one particular embodiment of the invention, administration of 1F7 can break the clonal dominance of ineffective anti-HCV antibodies and promote a broader, more effective antibody response.

HCV is a plus sense RNA virus that establishes chronic infection in up to 80% of exposed individuals. Long-term infection can lead to liver cirrhosis and hepatocellular carcinoma. There is no vaccine and current treatments are often ineffective. The ability of HCV to mutate key determinants and escape immune selection pressures exerted by antibodies and T cells is important for the establishment of chronic infection. As in HIV infection, the immune system may become locked into recognition of the original infecting strain of HCV and can be unable to adapt to subsequent mutations. Antibodies against a particular region of the HCV E2 protein termed the hypervariable region 1 (HVR1) are believed to be important for preventing new infection of cells and promoting clearance of viral infection.

Thus, an antibody, or antigen binding franment or derivative, broadly responsive against HCV E2 HVR1 would be expected to provide better protection against HCV mutants and would be expected to be associated with a more favorable outcome of infection. Expression of a common idiotype on antibodies against a particular antigen may be associated with a narrow antibody response against that antigen; a situation which has been termed "clonal dominance". Clonal dominance can weaken the adaptation of the immune response to emerging viral mutants and favor viral persistence.

As used herein, the term "HCV-related disease" refers to both asymptomatic and symptomatic phases, which follow HCV infection. HCV infection is characterized by flu-like symptoms and can evolve to a chronic infection, liver cirrhosis, and hepatic carcinoma. As used herein, the term "antibody" refers to any molecule which has specific immunoreactivity, whether or not coupled with another compound, such as a targeting agent, carrier, label, toxin, or drug. Although an antibody usually comprises two light and two heavy chains aggregated in a "Y" configuration with or without covalent linkage between them, the term is also meant to include any reactive fragment or fragments of the usual composition, such as Fab, F(ab')$_2$, F(ab') proteins, or single chain polypeptides having binding affinity for an antigen.

As used herein, the term "idiotope" or idiotypic determinant refers to an antigenic determinant or epitope unique to the immunoglobulin product of a single clone of cells. The idiotope is found in the variable region of the antibody. The term "epitope" refers more generally to an antigenic determinant on a molecule which is recognized by antibodies. The term "anti-idiotypic" or "anti-idiotypic antibody" refers to an antibody raised against a first antibody which specifically binds to an idiotope of the first antibody.

As used herein the term "specifically" is used interchangeably with the terms "specific reactivity" "specifically reactive" and "inimunoreactivity." Each term refers to a binding affinity which is greater than background binding. For example, a binding affinity that is measured b an optical density of greater than the standard deviation of the mean optical density of a control as determined by conventional ELISA techniques is considered to represent specific immunoreactivity. Other assays known in the art can also be used to determine specific reactivity. The term "not significantly reactive" is a binding affinity which is not greater than background binding.

As used herein the term "clonotype" refers to the homologous product of a clone of cells, or the phenotype of a clone of cells. Idiotypic determinants exprssed by populations of antigen-specific B cells or T cells seve as clonotypic markers for immune cells responding to a given antigenic challenge. Clonotypic specificities can be linked to a single epitope specificity or can be shared by antibodies of different specificities (Zhou et al., *J. Immunol.* 145:2554. Elimination of the B cells responsible for clonal dominance allows recruitment of new B cell clones producing antibodies more appropriate for the mutated virus. When the dominant cells share a common idiotype, this can be achieved by administration of anti-idiotypic antibodies, and the like, against that common idiotype.

As used herein, the term "idiotope" or idiotypic determinant refers to an antigenic determinant or epitope unique to the immunoglobulin product of a single clone of cells. The idiotope is found in the variable region of the antibody. The term "epitope" refers more generally to an antigenic determinant on a molecule which is recognized by antibodies. The term "anti-idiotypic" or "anti-idiotypic antibody" refers to an antibody raised against a first antibody which specifically binds to an idiotope of the first antibody.

The term "specificity" as used herein is used interchangeably with the terms "specific reactivity" "specifically reactive" and "immunoreactivity". Each term refers to a binding affinity which is greater than background binding. For example, a binding affinity that is measured by an optical density of greater than the standard deviation of the mean optical density of a control as determined by conventional ELISA techniques is considered to represent specific reactivity. Other assays known in the art may also be used to determine specific reactivity. The term "not significantly reactive" is a binding affinity which is not greater than background binding.

As used herein the term "clonotype" refers to the homologous product of a clone of cells, or the phenotype of a clone of cells. Idiotypic determinants expressed by populations of antigen-specific B cells or T cells serve as clonotypic markers for immune cells responding to a given antigenic challenge. Clonotypic specificities may be linked to a single epitope specificity or may be shared by antibodies of different specificities (Zhou, et al. *J. Immun.* 145, 2554 (1990)).

The present invention provides a compound which is specifically reactive with more than one type of antibody specific for a virus which causes a chronic infection, i.e., HCV, HIV, SIV and the like, and not specifically reactive with antibodies non-specific for antibodies reactive with a virus which causes a chronic infection. In particular, the present invention provides an anti-idiotypic antibody which is specifically reactive against an idiotope common to more than one type of human antibody specific for HCV, HIV and SIV, and not specifically reactive with human antibodies non-specific for HCV, HIV or SIV. A preferred anti-idiotope antibody is the monoclonal antibody 1F7, which specifically reactive with a common clonotype shared by anti-HIV antibodies and anti-HCV antibodies having different specificities.

The anti-idiotypic antibody useful in the methods of the present invention can be used as a diagnostic and prognostic marker to measure the level of reactive HCV antibodies in samples from HCV-infected patients. Analysis of these levels allows early characterization of HCV-related disease progress, allowing the early diagnosis and treatment of HCV-related pathologies. In addition, the anti-idiotypic antibody is useful therapeutically to facilitate viral clearance. Dominant B-cell clones producing antibodies which express the idiotope against which the antibody is reactive and which are no longer effective against HCV are suppressed, thereby restoring the normal polyclonal immune response which can effectively clear the virus from the infected individual's system.

The anti-idiotypic antibody useful in the methods of the present invention was produced against HIV-infected sera, and then screened for specific reactivity against antibodies reactive against various HIV antigens, and for lack of reactivity against human non-HIV antibodies. The anti-idiotypic antibody has now also been demonstrated to be specifically reactive with antibodies reactive against different HCV antigens, such as anti-NS3 antibodies, anti-NS4 antibodies and antibodies specific for the putative principle neutralizing determinant HCV E2 HVR1 (Id$^+$).

Antibodies similar to 1F7 having the characteristics required for the antibodies useful in the methods of the present invention, i.e., binding specificity for the idiotope recognized by the monoclonal antibody 1F7, can be produced by methods well known in the art. For example, antibodies may be produced by monoclonal techniques such as the method of Kohler and Milstein, *Nature* 256, 495 (1975), which may be modified by Gerhard, *Monoclonal Antibodies*, Kennett et al., eds., 370-371 (1980), for example, both of which are incorporated herein by reference. Alternatively, antibodies can be screened from polyclonal selections by well-known assay methods. In addition, Fabs and methods for making them are described in Harlow and Lane, *Antibodies. A Laboratory Manual*, 626-631 (1988), which is incorporated herein by reference. Examples of reactive single chain polypeptides and a method to generate them are taught by Ladner, U.S. Pat. No. 4,946,778, which is incorporated herein by reference. Antibodies can also be produced by recombinant DNA techniques such as those taught by Cabilly et al., U.S. Pat. No. 4,816,567, for example, which is herein incorporated by reference, or selected from immunoglobulin combinatorial libraries as taught, for example, by Huse, et al., *Science* 246, 1275 (1989), which is also incorporated by reference. CDR grafting as taught, for example, by Cabilly et al., supra, can also be used to produce fragments reactive with the idiotope. The nucleotide sequences and amino acid sequences for the light and heavy chains of the monoclonal antibody 1F7 useful for making various recombinant binding proteins, such as single chain antibodies, CDR grafted immunoglobulins, and the like, have been disclosed in U.S. Pat. No. 6,057,421 (incorporated herein by reference in entirety).

In addition, the invention provides an isolated idiotope found to be common to several types of antibodies specific to viruses causing chronic infection, ie., HIV, HCV, and the like, particularly those produced by dominant restricted B-cell clones, and specifically reactive with the anti-idiotypic antibody 1F7 as demonstrated to be useful in the methods of the present invention. This idiotope, when recognized and isolated from an Id$^+$ antibody, or otherwise synthetically or recombinantly produced, is useful in the production of monoclonal and polyclonal antibodies for diagnostic, prognostic and therapeutic applications using techniques well known in the art. For example, the isolated idiotope can be used to immunize animals to generate hybridomas expressing monoclonal antibodies specific for the idiotope. In other cases, the idiotope can be used to stimulate an immune response in an animal, i.e., a rabbit, goat, non-human primate or other animal from whose serum polyclonal antibodies can be obtained by methods well known in the art.

Further, the idiotope can be used for the purification or characterization of anti-idiotypic antibodies of interest, for example, monoclonal antibodies or antibodies present in human tissue or body fluids. In addition to antibodies, the methods of the present invention can employ non-antibody compounds which have a binding affinity for the idiotope recognized by the 1F7 antibody, and which do not bind to non-HCV antibodies. Such compounds can be constructed according to methods known in the art and include peptide or non-peptide drugs, for example, which have a specific binding affinity for the recognized idiotope.

In particular, peptides having the binding affinity for the idiotope recognized by the 1F7 antibody can be made by altering heavy and/or light chain amino acid sequence of the variable domain of 1F7 antibody by substitutions, additions or deletions that provide for functionally equivalent molecules. Due to the degeneracy of nucleotide coding sequences, other DNA sequences which encode substantially the same amino acid sequence as a 1F7 monoclonal antibody gene, for example, as disclosed in U.S. Pat. No. 6,057,421, incorporated herein by reference, can be used in the practice of the present invention. These include, but are not limited to, nucleotide sequences comprising all or portions of a 1F7 monoclonal antibody heavy and/or light chain gene which is altered by the substitution of different codons that encode a functionally equivalent amino acid residue within the sequence, thus producing a silent change. Likewise, the 1F7 derivatives of the invention include, but are not limited to, those containing as a primary amino acid sequence all or part of the amino acid sequence of a 1F7 heavy or light chain variable region including altered sequences in which functionally equivalent amino acid residues are substituted for residues within the sequence resulting in a silent change.

For example, one or more amino acid residues within the sequence can be substituted by another amino acid of a similar polarity which acts as a functional equivalent, resulting in a silent alteration. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The present invention provides a method of restoring oligoclonality in the antibody response to HIV infection through the administration of the anti-idiotypic antibody or other reactive compound of the present invention to an $HCV^+$ individual. Anti-idiotypic regulation can enforce oligoclonality either by suppressing the dominant B cell response to HCV or reinforcing the growth of other clones. This approach to treatment is based on the particular characteristics of HCV infection.

During the time HCV inhabits the host, its major neutralizing epitopes, particularly HCV E2 HVR1, undergo rapid mutations giving rise to neutralization-escape variants (Nara et al., *J. Virol*. 64:3779 (1990); Nara et al., *FASEB J.* 5:2437 (1991)). It is thought that the antibodies which were produced in response to the initial HCV infection are not effective against the new escape variants and that the host immune system fails to produce new antibodies to the variants (Montefiori et al., *Virology* 182:635 (1991); Nara et al. *J of Virol*. 64:3779 (1990); Nara et al., *Proc. Natl. Acad. Sci. USA* 84:797 (1987)). The failure of the immune system to recognize these newly-emerging virus isolates is thought to be due to the establishment of a dominant clonal population of B-cells committed, or restricted, to producing antibodies to the original HCV variant. The dominant clones prevent the recruitment and expansion of other B-cell populations which could be capable of an effective response to new HCV variants and other opportunistic viruses. In other settings, dominantly established B-cells have been found to exert a suppressive effect on minor B-cells which are directed against the same or cross-reactive epitopes (Askonas and Williamson, *Nature* 238:339 (1972); Briles and Davie *J. Exp. Med*. 152:151 (1980)).

It appears that as HCV generates neutralization escape variants, the mutated epitopes retain sufficient cross-reactivity to continue to trigger the early, clonally expanded B-cell clones. Evidence for this cross-reactivity with HIV envelope epitopes has been observed in divergent isolates (Kang et al., *Proc. Natl. Acad. Sci. USA* 88:6171 (1991)). Thus, B-cells with potentially higher affinity for mutated epitopes may be limited in their ability to respond and proliferate to reach an effective clone size. Instead, cross-stimulation by mutated HCV epitopes continues to trigger and expand the original and now ineffective clones. Recent reports on constant IEF profiles over time in HIV-1 infected individuals document the persistence of anti-gp120 specific B-cell clones (Matricardi et al., *Seventh International Conference for AIDS* 2:167 (1991)). By this mechanism a situation can develop in which the infected individual produces human neutralizing antibodies that are effective against laboratory strains and isolates from different seropositive individuals, but less effective against the autologous HCV variants as has been demonstrated for HIV-1 (Montefiori et al. supra, (1991); Nara, et al., supra (1990)).

The approach to treatment of HCV infection provided by the present invention is based on the surprising discovery that idiotope common to more than one type of virus which causes a chronic infection is not only apparently produced by restricted B-cell clones, as demonstrated previously for HIV infection, but also react with antibodies specific to different viruses. Similarities between the effects in HCV and HIV specific antibodies has been demonstrated by ELISA assays and kappa/lambda light chain analysis as demonstrated in the Example provided below.

A preferred anti-idiotypic antibody is the monoclonal 1F7 antibody. The production and screening of 1F7 has been described previously in U.S. Pat. No. 5,849,583, incorporated herein by reference in its entirety). A hybridoma cell line capable of expressing the 1F7 antibody has been previously deposited with the American Type Culture Collection, 10801 University Blvd., Manassas, Va. 20110-2209, and has been assigned ATCC No. HB 11286. 1F7 has been found to be specifically reactive with at least three anti-HIV antibodies having separate specificities. Further, it has previously been demonstrated that the 1F7 Id is a clonotype marker for anti-HIV antibodies. A clonotypic analysis of $HIV^+$ and $HIV^-$ sera demonstrated that it was common for the 1F7 Id clonotype to be shared by different anti-HIV-1 antibodies produced by the same $HIV^+$ individual.

In the present application, it has been demonstrated that this idiotype is shared by antibodies having specificity for different Hepatitis C Virus antigens including the antigen comprising a putative neutralizing epitope. Because a shared clonotypic marker on B cells responding to HIV or HCV infection would be expected to be the target of regulation and maintenance of the immune response to the HCV and/or HIV virus, the 1F7 Id is considered to be involved in anti-idiotypic regulation of the immune system in HCV and HIV-infected persons. Therefore, the present invention provides a method of overcoming the dominance of the ineffective clones by blocking the idiotype recognized by the anti-idiotypic antibody of the present invention. Treatment of a patient with the compound of the invention will result in the specific binding of the antibody or related compound to the idiotype on cells in the dominant clones. This results in the inhibition of their proliferation and curtailment of the production of antibodies to the original HCV variant. As a result of the dominant cells being blocked, other B-cells are able to respond to the new HCV variants. A normal polyclonal immune response is restored and antibodies to the new HCV variants are effective in clearing the virus from the host system.

Further T cells in $HCV^+$ infected persons can be subject to anti-idiotypic regulation via the idiotope recognized by 1F7. T cells from $HCV^+$ sera sample can be analyzed for evidence of anti-idiotypic regulation by the 1F7 anti-idiotypic antibody. For example, Peripheral Mononuclear Blood Cells (PMBC) can be taken from sera from $HCV^+$ individuals and HCV-normal control individuals and grown in culture according to the methods well known to the skilled artisan. These cells can be exposed to the 1F7 antibody and an isotype control antibody. The 1F7 antibody would be expected to induce apoptosis in the majority of $HCV^+$ samples, and in few or none of the HCV-control samples. Such a finding indicates that 1F7 binds a subset of T-lymphocytes selectively expanded in HCV infection through receptor molecules linked to cell-mediated apoptosis. Therefore, by selectively binding to subsets of B and T lymphocytes expanded during HCV infection, the antibody of the present invention is expected to favorably alter the immune response in HCV infection.

In another aspect of the present invention, the presence of the idiotope recognized by the antibody of the present invention in a sample of human sera can correlate with the occurrence of HCV-related pathologies in the individual. Therefore, the detection of the 1F7 idiotope by reaction with the 1F7 antibody is a method of predicting, detecting, or monitoring the occurrence of HCV related disease $HCV^+$ patients. The detection and diagnosis of HCV at an early stage is particularly useful because it allows for a more aggressive and suitable treatment.

The invention further relates to use of the antibody or non-antibody compound of the present invention to detect certain types of HCV antibodies in a sample. This can be useful for identifying HCV antibodies in cells or other samples being prepared for laboratory use, or in samples from patients suspected of having HCV-related disease. One embodiment involves contacting the sample suspected of containing HCV antibodies with the antibody or compound of the present invention and determining whether binding occurs. For example, a sample from a patient might be serum, semen, urine, tissue, cells or any other sample generally known or suspected to contain antibodies. A sample might also be spent culture from cell lines being tested for HCV antibody production. The antibody is most easily put in contact with the sample by mixing them together in a test tube or in the depression well of a slide. Subsequent determination of binding can be performed by any means known in the art, for example, radioimmune assay, staining of labeled compound, or immunoprecipitation. Binding affinity above background indicates the presence of HCV antibodies and is diagnostic of HCV-related disease.

In addition, the invention relates to the use of the antibody or non-antibody compounds of the present invention to obtain a quantitative determination of HCV antibody level in order to prognose a patient's HCV-related disease progression so that effective therapy can be initiated. As used herein, the term "prognose" of "prognosing" refers to monitoring the progression, determining the prognosis or forecasting the appearance of symptoms of HCV-related disease.

Previous methods of plotting antibody levels have proven unsatisfactory as sole prognostic tools. The levels of HCV antibody obtained by practicing the present invention are the result of the reliable, progressive development of clonal dominance of B-cell colonies. The antibodies produced by these colonies exhibit the novel idiotope and bind to the antibody or compound of the invention. Quantitative results regarding binding may be obtained as described above. The amount of binding determined by the procedure is compared to a standard for the various stages of HCV-related disease. In this way, it is possible to determine the stage of the patient's disease and prognose the development of further symptoms. The standard could be prepared, for example, by the methods described above using fluid samples from patients with symptoms known to characterize specific stages of HCV-related disease and determining the amount of HCV antibody specifically reactive with the antibody or Id-reactive compound of the invention. Resulting levels of antibody are charted against time correlating to stage of progression. The resultant chart serves as the standard on which results from patients of unknown diagnosis and prognosis are plotted. The stage of progression and prognosis of the patient's disease is determined by comparison of his level of HCV antibodies which react to the antibody or non-antibody compound compared to the standard. The 1F7 antibody of the present invention, for example, has been shown, for example, to be particularly precise in monitoring HCV-related disease.

The invention further relates generally to methods for the prevention, immunization and treatment of HCV-related disease by administering an effective amount of the compound to a patient diagnosed with HCV-related disease. An effective amount of antibody to treat HCV-related disease is the amount necessary to produce the effect of destroying clonal dominance of restricted B-cells or restricted or infected T cells, thus restoring a polyclonal immune response in the patient. The compound may be provided as a pharmaceutical composition containing an effective amount of the compound together with a physiologically acceptable carrier. This composition can be administered by any means known in the art, for example, intravenous, intramuscular, subcutaneous, intradermal, intraperitoneal, or by infusion.

The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Pharmaceutical compositions can take the form of solutions, suspensions, emulsion, tablets, pills, capsules, powders, sustained-release formulations, and the like. The composition can be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Examples of suitable pharmaceutical carriers are described in, for example, *Remington's Pharmaceutical Sciences*, by E. W. Martin. Such compositions will contain a therapeutically effective amount of the compound of the present invention, preferably in purified form, together with a suitable amount of carrier so as to provide a formulation proper for administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The agents of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The compound may also be bound to a suitable therapeutic agent such as a toxin, hormone, drug or other compound to facilitate the destruction of dominant B-cells. Drugs include, in general, alkylating agents, antiproliferative agents, tubulin-binding agents, cytotoxins, and the like. Toxins suitable as therapeutic agents include podophyophyllotoxins, ricin, the trichothecenes, the colchicenes and pseudomonas endotoxin.

Compositions useful in the methods of the invention, comprising an effective amount of a 1F7 monoclonal antibody in a pharmaceutically acceptable carrier, can be administered to a patient having a HCV-related disorder. The amount of antibody composition which will be effective in the treatment of a particular patient will depend on the nature of the disorder or condition of the patient, and can be determined by standard clinical techniques.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are intended to illustrate but not limit the invention. While they are typical of those that might be used, other procedures known to those skilled in the art may be alternatively employed.

EXAMPLE

In the following example the anti-idiotypic antibody 1F7 was demonstrated to bind to a number of antibodies specific for certain proteins of Hepatitis C virus isolated from several individuals.

Materials and Methods

Samples

Heparinized whole blood samples were obtained from individuals of known HIV status attending the St. John's General Hospital Infectious Diseases Clinic. Informed consent was obtained from each participant prior to blood collection and this study received ethical approval from the Memorial University Faculty of Medicine Human Investigation Committee. Whole blood was centrifuged at 500×g for 10 min and plasma was then removed and frozen in 500 µl aliquots at −70° C. until testing. An aliquot of each plasma sample was sent to the Newfoundland Provincial Health Laboratory for HCV antibody testing using the $2^{nd}$ generation Abbott recombinant immunoblot assay (RIBA). Fifteen HCV-seropositive plasma samples from HIV co-infected individuals and 4 HCV-seropositive plasma samples from non-HIV-infected individuals were identified. Additional plasma samples from each of these 15 individuals had previously been collected and stored for ongoing research and treatment studies related to their HIV infection.

Detection of Antibodies Against HCV Core, NS3, and NS4 Proteins

Immulon-2 ELISA plates (VWR Scientific, Mississauga, ON) were coated overnight at 4° C. with 50 ng/well of recombinant HCV core, NS3 or NS4 proteins (all from ViroGen Corporation, Watertown, Mass.) in 50 µl coating buffer (7.5 mM $Na_2CO_3$, 17.5 mM $NaHCO_3$, pH 9.2). Control wells were coated with 50 ng of trypsinogen (Sigma Chemical Co., St. Louis Mo.) as above. The following morning, the plates were washed 3 times with wash buffer (phosphate buffered saline (PBS), pH 7.2 with 0.1% Tween-20), and the wells blocked with 200 µl of 1% BSA (Sigma Chemical Co.) in wash buffer, for 1 hour. The plates were again washed 3 times and 100 µl plasma diluted 1/50 in dilution buffer (PBS with 0.1% BSA, 0.2% Tween 20 and 0.5% NP40) was added to duplicate wells for 90 min. The plates were then washed 6 times and alkaline phosphatase (AP)-conjugated goat-anti-human IgG (Jackson Labs, Mississauga, Ontario, Canada) diluted 1/3000 in dilution buffer was added for 60 min. After final 6 washes, 100 µl of AP substrate (1 mg/ml paranitrophenyl phosphate in 10% diethanolamine, 0.5 mM $MgCl_2$ buffer, pH 9.8) was added for 30 min. The optical density (OD) of each well was then read at 405 nm in a BioRad ELISA plate reader. Samples with a reading against the HCV protein of at least 0.2 OD units above that observed against trypsinogen under identical conditions were considered to have detectable antibodies against that HCV antigen.

Detection of Antibodies Against HCV E2 Hypervariable Region 1 (HVR1)

A consensus 18-mer peptide (SerHisThrValArg-GlyLeuThrSerLeuPheSer ProGlyAlaSerGlnAsn; SEQ ID NO: 1) was selected based on a previously published comparison of submitted HVR1 sequences (Chen et al., *Gastroenterol.* 116:135-143 (1999)) and on a study identifying synthetic "mimotopes" most likely to induce cross-reactive antibodies against multiple HVR1 sequences (Puntoriero et al., *EMBO J.* 17:3521-3533 (1988)). The HVR1-derived consensus peptide was synthesized by Genemed Synthesis Inc., South San Francisco Calif., $NH_2$-biotinylated and purified to >95% purity. To detect antibodies against the peptide, ELISA plates were first coated overnight at 4° C. with 1 µg of avidin (Jackson Labs). The next morning, the plates were washed 3 times and wells incubated with 100 ng of the HVR1 peptide (SEQ ID NO: 1) in dilution buffer for 90 min. or with buffer alone as a control. Dilution buffer for the plasma samples and antibody conjugates used in these assays contained 0.1% avidin in addition to the ingredients listed above. Diluted plasma samples were added and anti-HVR1 antibodies detected as described above.

Detection of the 1F7 Idiotype on Anti-HCV Antibodies

For samples with demonstrated reactivity against any or all of the HCV antigens, ELISAs were done to determine if the anti-HCV antibodies expressed the 1F7 idiotype. Plates were coated with HCV antigens, washed, blocked and incubated with diluted plasma samples as described above. After the plasma samples were washed off, duplicate wells were incubated for 90 min with either 250 ng of 1F7 or 250 ng of TEPC 183 (ICN Pharmaceuticals Inc., Aurora, Ohio), an IgM κ isotype control in 100 µl dilution buffer. Purified 1F7 was obtained from Immpheron Ltd. (Lexington, Ky.). Plates were then washed 6 times and incubated with 100 µl of a 1/5000 dilution of horseradish peroxidase (HRP)-conjugated goat anti-mouse IgM antibodies (Jackson Labs) in dilution buffer. The plates were then washed a final 6 times and incubated with 100 µl of HRP substrate (8 mg orthophenylenediamine/12 ml citric acid phosphate, pH 5.0 with 5 µl 30% $H_2O_2$ added immediately before use). Color was allowed to develop in the dark for 30 min and the reaction stopped by adding 50 µl 1N $H_2SO_4$ to each well. The OD was then read at 490 nm.

Estimation of κ/λ Ig Light Chain Ratio of Total Plasma IgG and Anti-HCV Antibodies For samples with demonstrated reactivity against any or all of the HCV antigens, ELISAs were done to estimate the ratio of κ/λ Ig light chain expression in anti-HCV antibody populations. A reference point for comparison with highly polyclonal IgG populations was established by estimating the ratio of κ/λ Ig light chain expression in total plasma IgG for each HCV-seropositive individual. To estimate the ratio of κ/λ Ig light chain expression in anti-HCV antibody populations, plates were coated with HCV antigens, washed and blocked as above. Plasma samples diluted 1/50 or higher as required, were incubated on the plates in quadruplicate. After washing, 1 duplicate set of wells was incubated for 1 hr with 100 µl of a 1/500 dilution of AP-conjugated mouse monoclonal antibody against human κ light chains (BD-Pharmingen, Mississauga, Ontario, Canada) and the other duplicate set of wells incubated with 100 µl of a 1/500 dilution of AP-conjugated mouse monoclonal antibody against human λ light chains (BD-Pharmingen). The plates were washed 6 times and AP substrate was added. Two OD readings at 405 nm were taken within the linear phase of color development and the κ/λ ratio estimated from the ratio of the slopes of OD increase with each developing reagent. For total plasma IgG, plates were coated with 250 ng of goat anti-human IgG (Jackson Labs) and plasma samples diluted between 1/20,000 and 1/100,000 in dilution buffer as necessary. If the κ/λ ratio of antibodies against any particular HCV antigen differed by >3 standard deviations from the mean estimated κ/λ ratio of total plasma IgG for all the HCV-seropositive individuals, the antibody population in question was considered skewed towards dominance of either κ or λ light chain bearing immunoglobulin molecules.

Results

Antibodies Against Individual HCV Antigens

Figure 3:
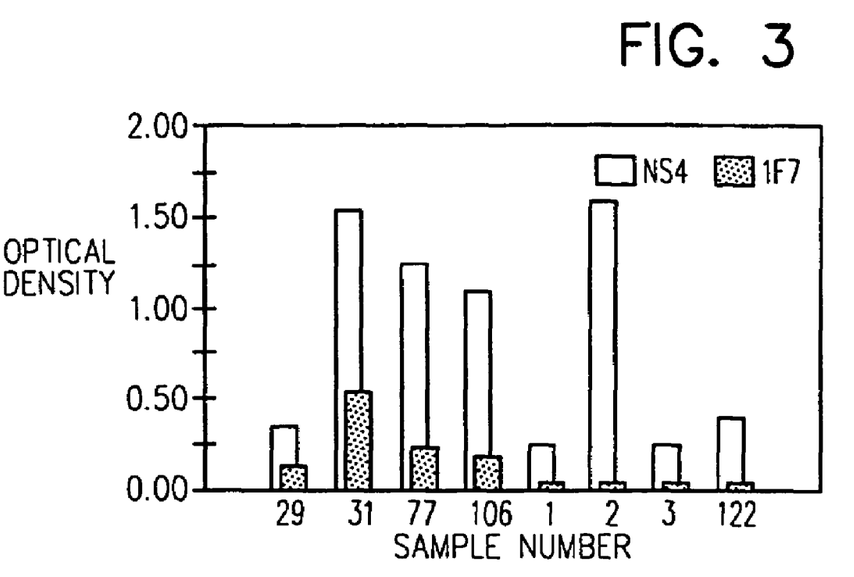
FIG. 3 depicts the expression of the 1F7 idiotype on anti-HCV NS4 antibodies in HIV/HCV co-infected individuals and HCV-infected individuals. Samples with detectable anti-HCV NS4 antibodies were tested by ELISA for reactivity of the anti-idiotypic 1F7 mAb with antibodies bound to NS4. Background reactivity against trypsinogen was subtracted from anti-HCV OD readings and reactivity with TEPC 183 was subtracted from the 1F7 OD readings.
Figure 4:
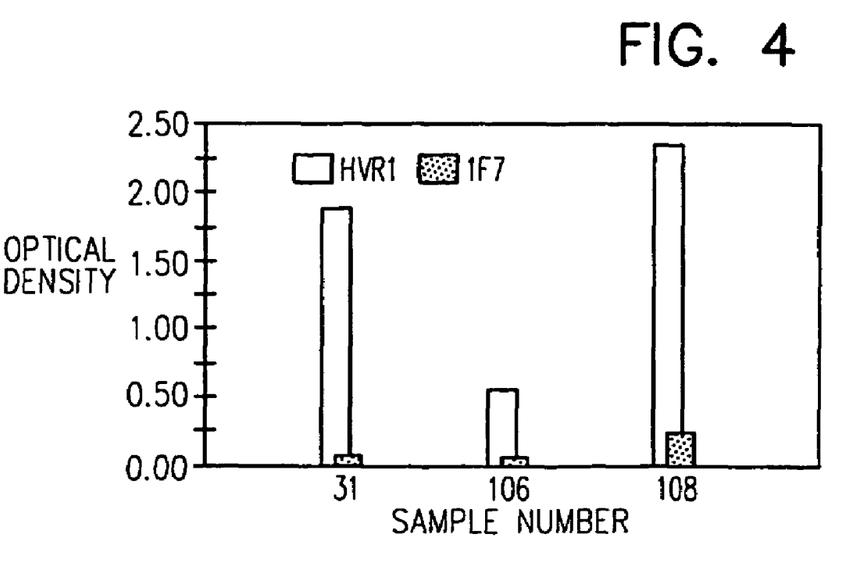
FIG. 4 depicts the expression of the 1F7 idiotype on anti-HCV E2 HVR1 antibodies. Three samples with detectable anti-HCV E2 HVR1 antibodies (all from HIV/HCV co-infected individuals) were tested by ELISA for reactivity of the anti-idiotypic 1F7 mAb with antibodies bound to the HCV E2 HVR1-derived peptide. Background reactivity against avidin was subtracted from anti-HCV OD readings and reactivity with TEPC 183 was subtracted from the 1F7 OD readings.

The first step in assessing 1F7 idiotype expression on anti-HCV antibodies was to characterize the antibody profile of the plasma samples against defined HCV antigens. Plasma samples from 15 HCV-seropositive HIV co-infected individuals and from 4 HCV-seropositive non-HIV-infected individuals (as determined by standard $2^{nd}$ generation diagnostic RIBA) were tested for antibody reactivity against recombinant HCV core, NS3 and NS4 antigens. All 19 samples were also tested against a consensus peptide from HCV E2 HVR1, the putative principal neutralizing determinant of HCV (Zhou et al. *Virology* 269:276-283(2000)). Antibodies against HCV core (16/19) (FIG. 1A) and NS4 (8/19) (FIG. 2) were most common and generally more prominent in terms of ELISA OD readings. Antibodies against HCV NS3 (6/19)(FIG. 3) and the synthetic peptide from HCV E2 HVR1 (3/19) were less common (FIG. 4).

Expression of the 1F7 Idiotype on Anti-HCV Antibodies

Figure 1A:
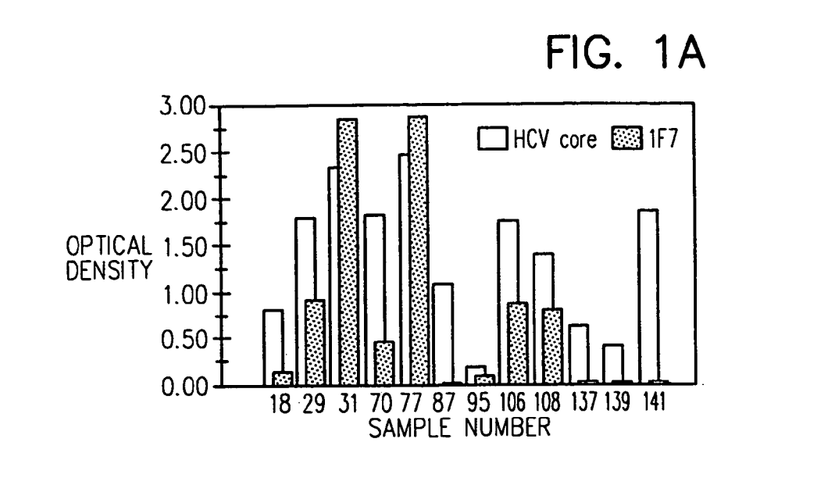
Figure 2:
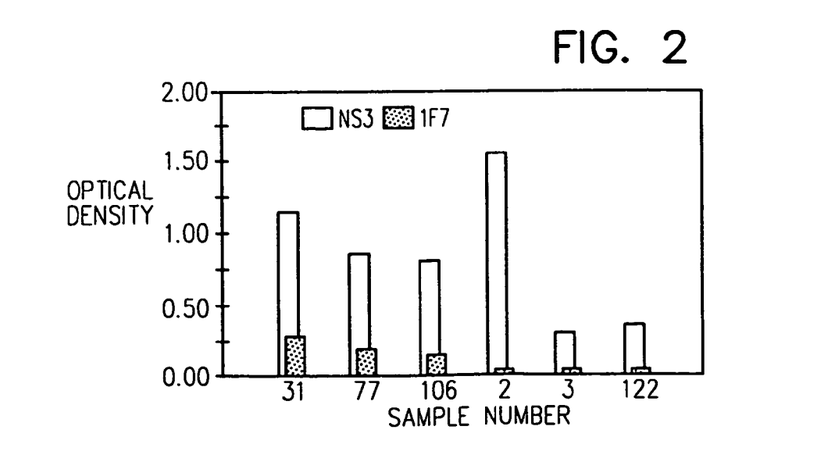
FIG. 2 depicts the expression of the 1F7 idiotype on anti-HCV NS3 antibodies in HIV/HCV co-infected individuals and HCV-infected individuals. Samples with detectable anti-HCV NS3 antibodies were tested by ELISA for reactivity of the anti-idiotypic 1F7 mAb with antibodies bound to NS3. Background reactivity against trypsinogen was subtracted from anti-HCV OD readings and reactivity with TEPC 183 was subtracted from the 1F7 OD readings.

Following characterization of the antibody reactivity of the samples against different HCV antigens, each individual's set of antibodies was tested against relevant HCV antigens for expression of the 1F7 idiotype. Seven out of 12 HIV co-infected individuals with detectable antibodies against HCV core expressed the 1F7 idiotype on their anti-HCV core antibodies (FIG. 1A). Three out of 4 and 3/3 HIV co-infected individuals with detectable antibodies against HCV NS4 and NS3 proteins respectively expressed the 1F7 idiotype on these anti-HCV antibodies (FIG. 1A, FIG. 2 and FIG. 3). One of the 3 HIV co-infected individuals with detectable antibodies against the HCV E2 HVR1-derived peptide expressed the 1F7 idiotype on these antibodies (FIG. 4). These data demonstrated that in HCV-infected individuals co-infected with HIV, selection of the 1F7 idiotype on anti-HCV antibodies, including potential neutralizing antibodies, occurred to a similar extent as selection of the 1F7 idiotype on anti-HIV antibodies (Wang et al., *Eur. J. Immunol.* 22:1749-1755 (1992)).

Figure 1B:
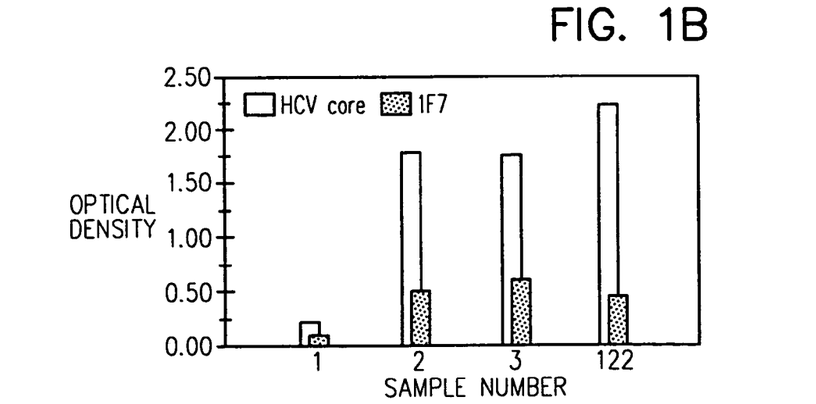
FIG. 1B depicts the expression in HCV-infected individuals. Samples with detectable anti-HCV core antibodies were tested by ELISA for reactivity of the anti-idiotypic 1F7 mAb with antibodies bound to HCV core. Background reactivity against trypsinogen was subtracted from anti-HCV core OD readings and reactivity with TEPC 183 was subtracted from the 1F7 OD readings.

Three of the 4 non-HIV co-infected individuals tested expressed the 1F7 idiotype on their anti-HCV core antibodies (FIG. 1B). None of the 4 expressed the 1F7 idiotype on their anti-HCV NS4 antibodies (FIG. 3) and 0/3 expressed the 1F7 idiotype on anti-NS3 antibodies (FIG. 2). None of the 4 had detectable antibodies against the HCV E2 HVR1-derived peptide. These data demonstrated that selection of the 1F7 idiotype on anti-HCV antibodies was independent of any concurrent selective influence exerted by HIV on the immune system. The overall observed prevalence of the 1F7 idiotype on anti-HCV antibodies the study (10/19) approached the reported prevalence of the 1F7 idiotype on anti-HIV and anti-SIV antibodies from different individuals (Wang et al., *Eur. J. Immunol.* 22:1749-1755 (1992); Grant et al., *Immunol. Cell Biol.* 174:38-44 (1996)).

κ/λ Ig Light Chain Ratios of Anti-HCV Antibodies

Figure 5:
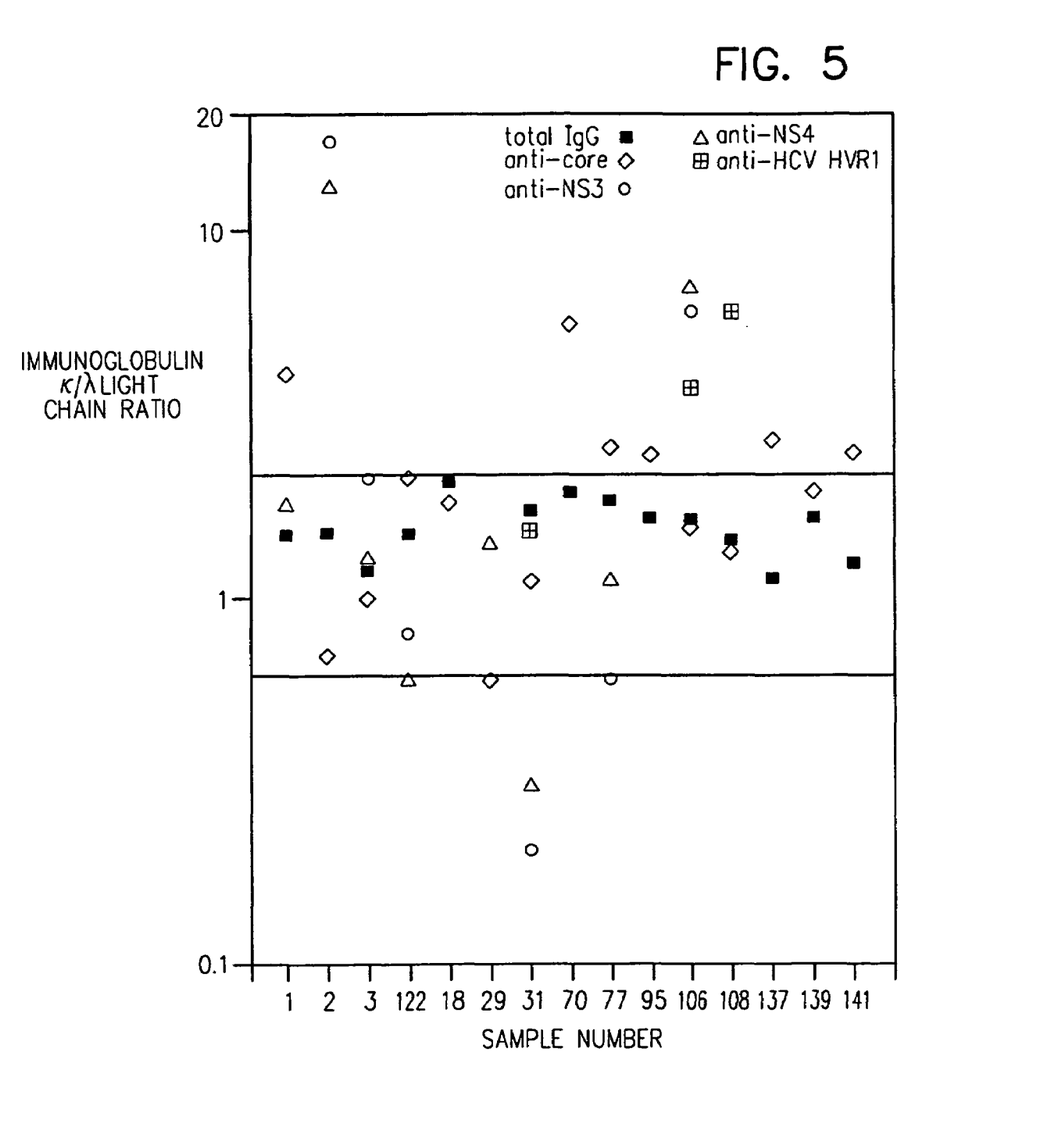
FIG. 5. Relative usage of immunoglobulin κ and λ light chains by anti-HCV antibody populations and total plasma IgG in HCV-infected and HIV/HCV co-infected individuals. The ratio of initial rates of increase in ELISA OD readings with ακ and λ specific development reagents was used to estimate relative usage of κ and λ light chains by plasma antibodies binding to HCV proteins coated on ELISA plates. The parallel horizontal lines within the graph plot frame indicate 3 standard deviations (SD) above and below the mean estimated κ/λ light chain ratio for total plasma IgG in the study group (0±SD=1.52±0.265).

Immunoglobulin light chain usage of anti-HCV antibodies was studied to test whether the same association between 1F7 idiotype expression and restricted B cell involvement as was demonstrated for antibody responses against HIV was also apparent in the antibody response against HCV. To establish a normal reference range for the κ/λ light chain ratio in polyclonal plasma IgG and to ensure that any aberrant ratios were not due to systemic changes in Ig κ/λ light chain usage, the κ/λ Ig light chain ratio of total plasma IgG was estimated from each of the 19 HCV-seropositive individuals in this study (FIG. 5). The estimated κ/λ ratio for total plasma IgG was consistent throughout the study cohort ranging between 1.1 and 2.1 (mean±standard deviation=1.52±0.265). These data demonstrated that for the individuals in the study, neither HIV infection, HCV infection nor HIV/HCV co-infection greatly affected systemic Ig κ/λ light chain usage.

The κ/λ light chain ratio for antibodies against discrete HCV antigens was estimated in order to assess skewing towards predominance of κ or λ light chains within each individual's set of antibodies produced against distinct HCV antigens. A κ/λ ratio differing by more than 3 standard deviations from the mean κ/λ ratio calculated for total plasma IgG was considered skewed κ/λ light chain usage within that individual's antibody response to that particular HCV antigen. A skewed κ/λ ratio was found for the antibody response against at least 1 HCV antigen for 2/4 non-HIV co-infected individuals and 9/11 HIV co-infected individuals tested. Skewing in favor of both κ and λ chain dominance was observed, but κ chain predominance was more common. Skewing of the κ/λ ratio of the antibody response against the putative principal neutralizing determinant of HCV was observed in 2 out of 3 cases (FIG. 5). These data demonstrated that selective dominance of κ or λ Ig light chain usage within the humoral immune response against HCV, including in sets of potentially neutralizing antibodies, is quite common. The skewed κ/λ chain usage associated with expression of the 1F7 idiotype on anti-HCV antibodies is consistent with a restricted antibody response against HCV in HCV-infected individuals.

DISCUSSION

Although they are genetically unrelated, have different patterns of cellular tropism and induce distinct disease sequelae, HCV and HIV share important features relevant to their interactions with host immune systems. Both commonly establish chronic infections, at least in part because of mistake-prone RNA polymerases that generate a high mutation rate during viral replication (Bebenek et al., *J. Biol. Chem.* 264:16948-16956 (1989); Ogata et al., *Proc. Natl. Acad. Sci. USA* 88:3392-3396 (1991)). These mutations produce viral variants and immune selective pressure favors outgrowth of those variants poorly neutralized by anti-viral antibodies concurrently present in the host. The less diverse the neutralizing antibody response, the easier viral escape occurs through random mutations within neutralization epitopes. Since random mutations can't be anticipated by the immune system, adaptation of the immune response lags behind the virus and chronic infection ensues. Mutating viruses also exploit a phenomenon known as "original antigenic sin", in which the immune system commits itself to the viral variant initially present and continues to make antibodies against the image of this virus even when the virus now present has effectively shed this image (Webster, *J. Immunol.* 97:177-183 (1996)). Although some level of cross-reactivity with emergent viruses may explain persistence of the seminal antibodies, what stops the immune system from producing high affinity neutralizing antibodies against emergent viral variants is not clear.

In the case of HIV infection, original antigenic sin manifests as B cell clonal dominance, where the original responding B cells are locked in through a process termed "deceptive imprinting" or a "repertoire freeze" (Kohler et al., *Immunol. Today* 15:475-478 (1994)). This clonal dominance involves restricted diversity in the set of antibodies produced against HIV and is associated with expression of a common idiotype on anti-HIV antibodies with different specificities (Kohler et al., *Immunol. Today* 15:475-478 (1994); Kohler et al., *Immunologist* 3:32-34 (1995)). The current study demonstrated that these conditions are closely paralleled in the humoral immune response against HCV and more surprisingly, that the same common idiotype reported in association with clonal dominance in HIV infection is expressed on anti-HCV antibodies with different specificities. These new findings regarding the humoral immune response against HCV have significant implications for the pathogenesis of HCV disease and broader implications for the structure and function of idiotypic networks.

The frequency of 1F7 idiotype expression and of abnormal κ or λ light chain dominance on sets of antibodies produced against HCV proteins is consistent with a clonally restricted antibody response. Although only 3 of 19 plasma samples tested had detectable antibodies against the HCV E2-derived peptide we selected, these potentially neutralizing sets of antibodies (Zhou et al., *Virology* 269:276-283 (2000)) also showed evidence of light chain skewing and 1F7 idiotype expression. Peptides representing many other HCV variants would have to be synthesized to characterize potentially neutralizing antibodies present in the other samples, however, the low cross-reactivity observed with the consensus peptide is itself indicative of restricted neutralizing antibody responses. Such restricted responses, especially in the context of clonal or idiotypic dominance would favor immune escape and chronic infection with HCV, as with HIV.

The question of how expression and selection of the 1F7 idiotype overlaps both different species and unrelated chronic pathogens is theoretically intriguing. A somewhat analogous situation was previously reported with regard to the 16/6 idiotype, which unlike 1F7 is associated with a particular heavy chain V gene family (Schwartz and Stollar, *J. Clin. Invest.* 75:321-325 (1985)). This idiotype was first defined on a monoclonal anti-DNA antibody and later on other autoantibodies and anti-microbial antibodies (Shoenfeld et al., *J. Clin. Invest.* 70:205-208 (1982); Konikoff et al., *Clin. Immuol. Immunopathol.* 43:265-273 (1987)). Expression of this idiotype is associated with systemic lupus erythematosus (SLE) in humans and injection of antibodies bearing this idiotype into mice induced SLE-like symptoms (Mendlovic et al., (1988); Blank et al., *Scand. J. Immunol.* 31:45-52 (1990)). Pathogenic immune complexes in both situations contain 16/6 idiotype+ antibodies, fueling speculation that 16/6 can act as a pathogenic idiotype to perturb the regulatory network in such a way as allows autoimmunity to develop (Reviewed by Shoenfeld et al., *Clin. Immunol. Immunopathol.* 4:277-287 (1989)). Antibodies with common patterns of autoreactivity also emerge in chronic inflammatory conditions such as HIV infection, graft versus host disease and lepromatous leprosy (Grant et al., *J. Immunol.* 144:1241-1250 (1990)). This suggests that the immune system is predisposed to respond along certain autoreactive axes when chronically stimulated and there has been speculation that chronic pathogens can selectively activate responses along autoreactive axes to divert the immune system from more effective anti-microbial responses (Cohen, *Immunol. Today* 13:490-494 (1992)). If true, there may be therapeutic value in steering the immune response away from such fruitless axes.

In the SHIV model of HIV infection, administering 1F7 to SHIV-infected animals expressing the 1F7 idiotype on their anti-SHIV antibodies "thawed" the frozen B cell repertoire. Relief from clonal dominance was illustrated by a broadening of the HIV neutralizing antibody response to encompass viruses distinct from the inoculating strain together with an increase in neutralization titer against the inoculating strain (Muller et al., *Proc. Natl. Acad. Sci. USA* 95:276-281 (1998)). There is some controversy about the role of anti-HIV antibodies in protection from infection or modulation of chronic HIV infection, but if 1F7 treatment broadens and strengthens the neutralizing antibody response against HCV, this could have a more significant impact on the pathogenesis of HCV disease. All the characteristics of the antibody response against HCV suggest that administration of 1F7 could have a desirable effect in HCV infection.

To date, the 1F7 idiotype has been found on antibodies against 3 chronic pathogens, HIV, SIV and HCV, suggesting that all 3 selectively activate antibodies along a particular idiotype axis or that chronic stimulation itself drives selection of the 1F7 idiotype. Since uninfected volunteers receiving HIV gp120 vaccination express the 1F7 idiotype on their anti-HIV antibodies, the idiotype appears to be selected in the initial response to HIV and to persist throughout infection. Thus, it was originally thought that selection of the 1F7 idiotype might spread to anti-HCV antibodies in HIV/HCV co-infected individuals. On the contrary, the 1F7 idiotype was found on anti-HCV antibodies in non-HIV-infected individuals. The presence of 1F7 idiotype on such a diverse set of antiviral antibodies illustrates that B cells expressing $Ab_2$ recognizing the 1F7 idiotype have very high connectivity within the B cell repertoire. Such high connectivity would tend to suppress activation of the regulatory $Ab_2$-bearing B cells and favor assumption of clonal dominance by the responding 1F7 idiotype$^+$ B cells. However, the probability of chronic pathogens evolving determinants on so many individual proteins to take advantage of this structural feature of B cell networks seems remote. One alternative possibility is that the initial antibody response to HIV gp120 represents a special case, by virtue of gp120 acting as a B cell superantigen. It has been demonstrated that gp120 binds a broad set of immunoglobulin molecules based on the heavy chain V gene family expressed (Berberian et al., *Science* 261:1588-1591 (1993)). Such polyclonal activation would assure activation of clones expressing the 1F7 Idiotype and the high connectivity of the potential regulatory anti-idiotype would free the 1F7$^+$ B cells to establish clonal dominance. In the case of the other HIV and HCV antigens that select for 1F7 Idiotype expression, a more gradual process of selection would be expected.

This proposed pattern of idiotypic focusing can have adaptive as well as negative implications for the immune system. While freezing potential neutralizing antibody responses against a mutating pathogen is clearly a disadvantage, localizing chronic B cell activation within a limited region of idiotypic space could protect against immunopathology and leaves a more extensive B cell repertoire free to respond against unrelated pathogens. It remains to be determined how widespread 1F7 idiotype expression is on antibodies against other chronic pathogens and on autoantibodies.

All publications and patent documents cited in this application are incorporated by reference in their entirety for all purposes to the same extent as if each individual publication or patent document were so individually denoted.

What is claimed is:

1. A method for detecting human anti-HCV antibodies having a common idiotope comprising the steps of:

a) contacting a biological sample isolated from an individual with a HCV antigen to form an antibody-antigen complex;

b) contacting the antibody-antigen complex with the anti-idiotopic antibody 1F7 (ATCC Accession No. HB 11286) or binding fragments thereof having specific reactivity with an idiotope common to antibodies reactive with viruses which lead to chronic infection under conditions conducive to form an immune complex;

c) determining the presence of formed complex, wherein the presence of complex formation indicates the detection of human anti-HCV antibodies having a common idiotope.

2. The method of claim 1, wherein the binding fragment is a Fab, or a single chain antibody polypeptide.

3. The method of claim 1, wherein the biological sample is serum, semen, urine, tissue, cells or spent cell culture.

4. The method of claim 1, wherein the 1F7 antibody is labeled.

5. The method of claim 4, wherein the label is a radioactive label.

* * * * *